(12) United States Patent
Capobianco, Jr. et al.

(10) Patent No.: US 12,203,884 B2
(45) Date of Patent: *Jan. 21, 2025

(54) FLOW-THROUGH ELECTROCHEMICAL DETECTION SYSTEM

(71) Applicant: The United States of America, as Represented by the Secretary of Agriculture, Washington, DC (US)

(72) Inventors: Joseph A. Capobianco, Jr., Wyndmoor, PA (US); Andrew G. Gehring, Marlton, NJ (US); Cheryl M. Armstrong, Wyndmoor, PA (US); Joseph Lee, Flemington, NJ (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 563 days.

This patent is subject to a terminal disclaimer.

(21) Appl. No.: 16/682,719

(22) Filed: Nov. 13, 2019

(65) Prior Publication Data
US 2020/0300801 A1     Sep. 24, 2020

Related U.S. Application Data

(60) Provisional application No. 62/821,624, filed on Mar. 21, 2019.

(51) Int. Cl.
*G01N 27/327*     (2006.01)
*B01D 53/32*      (2006.01)
(Continued)

(52) U.S. Cl.
CPC .......... *G01N 27/327* (2013.01); *G01N 33/53* (2013.01); *G01N 33/6803* (2013.01); *B01D 53/326* (2013.01); *B01D 2313/18* (2013.01)

(58) Field of Classification Search
CPC .. G01N 27/327; G01N 33/53; G01N 33/6803; B01D 53/326
See application file for complete search history.

(56) References Cited

U.S. PATENT DOCUMENTS

| | | | |
|---|---|---|---|
| 7,087,148 B1 * | 8/2006 | Blackburn | B82Y 30/00 205/452 |
| 2005/0136500 A1 | 6/2005 | Yang et al. | |

(Continued)

FOREIGN PATENT DOCUMENTS

| | | | | |
|---|---|---|---|---|
| KR | 1020160021673 | * | 8/2014 | G01N 27/30 |
| WO | WO-9628538 A1 | * | 9/1996 | G01N 21/66 |

OTHER PUBLICATIONS

Fragoso et al. Electrochemical immunosensor for detection of proteic cancer markers . . . Chapter 33, Biosensors and molecular technologies for cancer diagnostics. 2012, pp. 573-590. (Year: 2012).*

(Continued)

*Primary Examiner* — Shafiqul Haq
(74) *Attorney, Agent, or Firm* — John D. Fado; Richard D. Tuminello

(57) ABSTRACT

A flow-through electrochemical detection system determines if an analyte is present in a sample. This system contains, at a minimum, an assay reaction chamber that contains a porous working electrode to which analyte capturing molecules are bound. As a sample passes through the working electrode, any analyte present in the sample binds to the analyte capturing molecules. After the sample passes through the flow-through electrochemical detection system, analyte detectors are placed inside the assay reaction chamber and bind to any analyte present. The analyte detectors contain a means for generating an electric current when exposed to a chemical or an enzyme. A potentiostat con- (Continued)

nected to the working electrode measures that generated current, thereby detecting the presence and quantity of the analyte in that sample.

14 Claims, 13 Drawing Sheets

(51) Int. Cl.
*G01N 33/53* (2006.01)
*G01N 33/68* (2006.01)

(56) References Cited

U.S. PATENT DOCUMENTS

| | | |
|---|---|---|
| 2010/0000881 A1 | 1/2010 | Franzen et al. |
| 2010/0173305 A1 | 7/2010 | Reshatoff et al. |
| 2014/0274805 A1 | 9/2014 | Wohlstadter et al. |
| 2014/0287411 A1 | 9/2014 | Reshatoff et al. |
| 2017/0111202 A1 | 4/2017 | Kim et al. |
| 2018/0015474 A1 | 1/2018 | Arlett et al. |

OTHER PUBLICATIONS

L. Beaudet, et al., 2001 "Homogeneous assays for single-nucleotide polymorphism typing using AlphaScreen," Genome Res. 11(4): 600-608.

D. Dressman, et al., 2003, "Transforming single DNA molecules into fluorescent magnetic particles for detection and enumeration of genetic variations," Proc. Natl., 8817-8822.

P. Glaser, et al., 2001, "Comparative genomics of *Listeria* species," Science 294(5543): 849-852.

R.F. Wang, et al., 1992, "16S rRNA-based probes and polymerase chain reaction method to detect Listeria monocytogenes cells added to foods," Applied and Env. 2827-2831.

C-H Yi, et al., 1996, "Improvement of polymerase chain reaction methods for rapid detection of Listeria monocytogenes in raw milk," Korean J. Vet. Res. 36(1):119-129.

* cited by examiner

FLOW-THROUGH ELECTROCHEMICAL DETECTION SYSTEM

CROSS-REFERENCE TO RELATED APPLICATIONS

The current patent application based on U.S. Provisional Patent Application No. 62/821,624, filed on Mar. 21, 2019, which is hereby incorporated by reference herein in its entirety.

BACKGROUND OF THE INVENTION

Field of the Invention

The invention pertains to a highly sensitive detection system that can determine an analyte's presence in a sample using a chemical or enzymatic reaction that generates a measurable electric current when the analyte is present. The analyte can be microorganisms, animal cells, plant cells, cell fragments, polynucleotides, proteins, small molecules/chemicals, and biomarkers that are indicators of the analyte. The sample traverses through a porous electrode to which analyte capturing molecules are attached and which bind the analyte. Because large quantity of the sample can pass through the porous membrane, minute quantities of an analyte in the sample are able to be captured by the system and thereby are detected.

Description of Related Art

In the food safety and water safety industries, the goal is zero tolerance for contaminants, especially harmful microorganisms, proteins, and/or chemicals to be present in food and water. Most devices or systems that detect contaminants are not sufficiently sensitive to conclude definitively that the sample is free from contaminants. One problem with many devices or systems is that these devices or systems fail to assay a sufficiently large quantity of the food or water to detect minute quantities of the contaminants, but those minute quantities can be extremely harmful to animals, including humans. Some devices or systems may be sufficiently sensitive but are extremely expensive to operate and take too long to determine the safety of the sample.

Prior art devices including PCR and immunoassays systems utilize a variety of well-known assays to detect analytes in a sample. Usually an analyte capturing molecule is part of these assays. Enzyme-Linked Immunosorbent Assay ("ELISA") is one well-known assay. ELISAs can be, for example, "sandwich" assays, "dot blot" assays, and "dipstick" assays. Color, luminescence, or fluorescence can be used to indirectly indicate the presence of the analyte in a sample. Another type of assay utilizes DNA or RNA oligonucleotides (the analyte capturing molecules) to bind to DNA or RNA oligonucleotides or polynucleotides (the analyte) in the sample and then utilizes polymerase chain reaction (PCR) to amplify the captured analyte and detect its presence in the sample. Another prior art assay involves using aptamers (oligonucleotides or polypeptides that have a specific three-dimensional shape) (the analyte capturing molecules) to bind to and capture a specific analyte in a sample. See, e.g., Lakhin, et al., *Acta Naturae*, 5(4):34-43 (2013) regarding oligonucleotide aptamers, and Colas, et al., *Nature*, 380(6574):548-50 (1996) regarding peptide aptamers. In yet another assay, microorganisms that naturally express proteins or other molecules on their surface that can bind to an analyte are used as the analyte capturing molecules. In a related assay, genetically altered microorganisms encode and produce surface proteins or other molecules that are exposed on the cell's exterior and can bind to an analyte. These microorganisms are used as analyte capturing molecules. These prior art assays may be highly specific for an analyte, but they have drawbacks, such as being unable to properly and effectively assay (i) large quantity of sample, (ii) samples containing particulate matter, and/or (iii) multiple types of analytes in a sample.

These prior art devices and/or systems also have limited sensitivity and are limited in the quantity of sample being tested because the sample is static; that is, the sample does not through the porous structure to which the analyte capturing molecule is attached. While some devices utilize a gold-mesh screen, it is difficult to clean the screen or remove the analyte capturing molecule and/or the analyte from the screen. Thus, it becomes expensive replacing the gold-mesh screen after performing each assay. Another problem with these prior art devices or systems is that they do not function well when particulate matter is present in the sample being tested (e.g., a slurry of ground beef, chicken, fish, etc.).

A need exists for a system that can detect minute quantities of an analyte in both large or small volumes, even when solid or liquid particles are present in the sample. The present system overcomes these prior art problems. It has high sensitivity with either large or small quantities of sample, with or without particulate matter (solids and/or liquids) being present in the sample. The system can be used to detect microorganisms (viruses, bacteria, protozoa, fungi, etc.), biopolymers such as polynucleotides (DNA, RNA, and synthetic nucleotides), polypeptides (proteins, protein fragments, toxins), and chemicals (drugs, explosives, carcinogens, allergens, pesticides, and synthetic and natural monomers).

BRIEF SUMMARY OF THE INVENTION

This disclosure is directed to a system for detecting an analyte in a sample. The system includes at least one assay reaction chamber in electrical communication with an electrical measuring device (preferably a potentiostat). A porous working electrode and a plurality of analyte-capturing molecules are positioned within the reaction chamber so that the plurality of analyte-capturing molecules is bound to the porous working electrode. The system is structured so that as a sample flows through the porous working electrode, the analyte-capturing molecules bind to any analyte present in the sample and generate an electric current that is transmitted to the potentiostat. The presence (or absence) and quantity of the electric current are indicative of the presence (or absence) and quantity of analyte in the sample.

BRIEF DESCRIPTION OF THE SEVERAL VIEWS OF THE DRAWINGS

As seen in FIG. 3, the assay reaction chamber 200 contains a glassy carbon electrode 260, a reference electrode 250, and a counter electrode 240 attached to the side of the assay reaction chamber. The glassy carbon electrode serves as the working electrode. The electrodes were connected via wires 190 to the potentiostat 160. A pipe 180 is connected to the assay reaction chamber's egress opening 220 and contains a flow control valve 140 downstream of the assay reaction chamber's egress opening 220.

FIG. 13 shows the current (in μA) for 5 ml and 60 ml samples containing E. coli O157:H7 in concentrations ranging from $10^2$ to $10^7$. Goat anti-E. coli Abs were previously bound to the working electrode. After passage of the E. coli containing sample through the flow-through electrochemical assay system, HRP-labeled goat anti-E. coli Ab with TMB and $H_2O_2$ is passed through the assay reaction chamber. Measurements represent the average values of three independent experiments. Error bars denote 1 standard deviation from the mean.

DETAILED DESCRIPTION OF THE INVENTION

The flow-through electrochemical assay system is a highly sensitive system for detecting the presence of an analyte in a sample. The analyte can be microorganisms (viruses, bacteria, protozoa, fungi, etc.), polynucleotides (DNA, RNA, or synthetic nucleotides), proteins/polypeptides, and chemicals. In one embodiment, the sample is a liquid which can be a solution or a suspension. For example, the sample can be homogenized food (raw or cooked;

obtained from plants or animals) in a liquid (water, oil, etc.), liquids obtained from the environment (e.g., water/liquid obtained from streams, rivers, lakes, oceans, rain, waste ponds, cooling ponds, mines, etc.), bodily fluids, homogenized bodily tissue, and even foods such as peanut butter, ice cream, etc. In brief, the sample suspected of containing an analyte traverses through the flow-through electrochemical assay system from a sample reservoir (if not present, then from wherever the sample is located into the first pipe), through an optional filter to remove large particulates, into the one or more assay reaction chambers where the sample traverses through a porous working electrode, and then to the waste reservoir. The assay reaction chamber contains a plurality of analyte capturing molecules attached to the porous working electrode. As the sample traverses through the porous working electrode, the analyte capturing molecules bind to the analyte (if any analyte is present).

Next, an analyte detector is added to the assay reaction chamber, and, if any analyte has bound to the analyte capturing molecules, then a chemical or enzymatic reaction occurs which generates an electric current. This electric current is detected, and one can determine if the analyte was present in the sample and the quantity present by comparing the generated electric current to known values.

Figure 1:
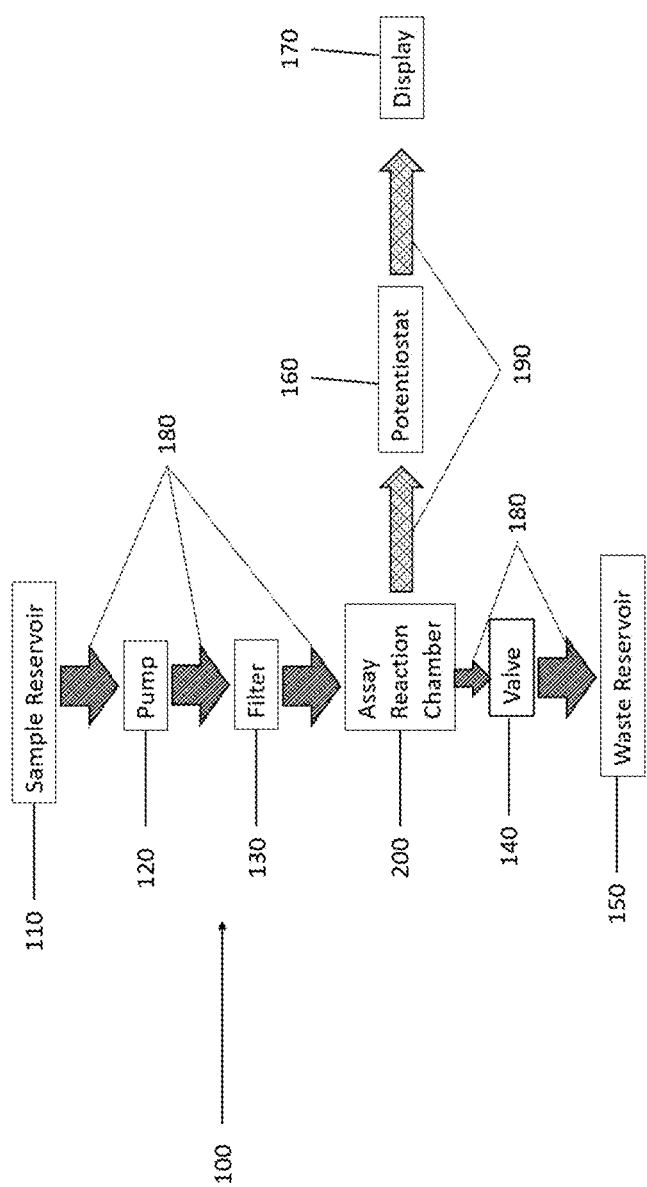
FIG. 1 shows a schematic of one embodiment of the flow-through electrochemical detection system 100. The flow-through electrochemical detection system 100 can contain a sample reservoir 110, a pump 120, a filter 130, an assay reaction chamber 200, a flow control valve 140, and a waste reservoir 150 in fluid connection with each other via pipes 180 (shown as arrows with diagonal lines). The flow-through electrochemical detection system 100 also can contain a potentiostat 160 and a display 170 in electronic communication with each other and with the assay reaction chamber 200 via connectors 190 (shown as arrows with cross-hatching).

As shown in the schematic in FIG. 1, in one embodiment, the flow-through electrochemical detection system 100 contains a sample reservoir 110, a pump 120, a filter 130, at least one assay reaction chamber 200, a flow control valve 140, and a waste reservoir 150, all of which are in fluid communication with each other via a plurality of pipes 180 (shown as arrows with diagonal lines) through which a sample passes. The assay reaction chamber 200 is in electronic communication with a potentiostat 160 which is in electronical communication with a display 170. As shown in FIG. 1, wires 190 (shown as arrows with cross-hatching) are the means used for this electronic communication between the assay reaction chamber 200, potentiostat 160, and display 170. Other known in the art means of electronic communication between these components can be used. In another embodiment, the pump 120 and filter 130 are optional. In another embodiment, the sample reservoir 110 can be the lake, river, stream, waste pond, cooling pond, mine, etc., rather than a distinct container holding a sample. As shown in FIG. 1, the flow control valve 140 is downstream of the assay reaction chamber 200, but in another embodiment the flow control valve can be upstream of the assay reaction chamber. The flow control valve 140 controls the sample's speed through the assay reaction chamber. The pump 120 forces the sample to move through the flow-through electrochemical detection system at a desired speed. The pump 120 may be located upstream or downstream of the at least one assay reaction chamber 200. In an alternate embodiment, the pump 120 can be a vacuum pump or a pneumatic or hydraulic driven piston, depending on the viscosity of the sample.

The flow-through electrochemical detection system 100 can have one assay reaction chamber 200 or multiple assay reaction chambers that are in parallel or series orientation to each other. If multiple assay reaction chambers are present, each assay reaction chamber is independently connected to the potentiostat. When multiple assay chambers are being used, each assay reaction chamber can assay for different analytes and would thus use different analyte capturing molecules and analyte detectors. Thus, the flow-through electrochemical detection system can assay for multiple analytes at the same time.

In one embodiment, the sample reservoir 100 induces sufficient pressure that the sample moves through the flow-through electrochemical detection system without need of a pump 120. In one embodiment, the assay reaction chamber 200 is of sufficient size to accommodate the sample's entire volume at one time. In another embodiment, the assay reaction chamber does not accommodate the sample's entire volume at one time, but the entire sample flows through the assay reaction chamber over a period of time.

Figure 2:
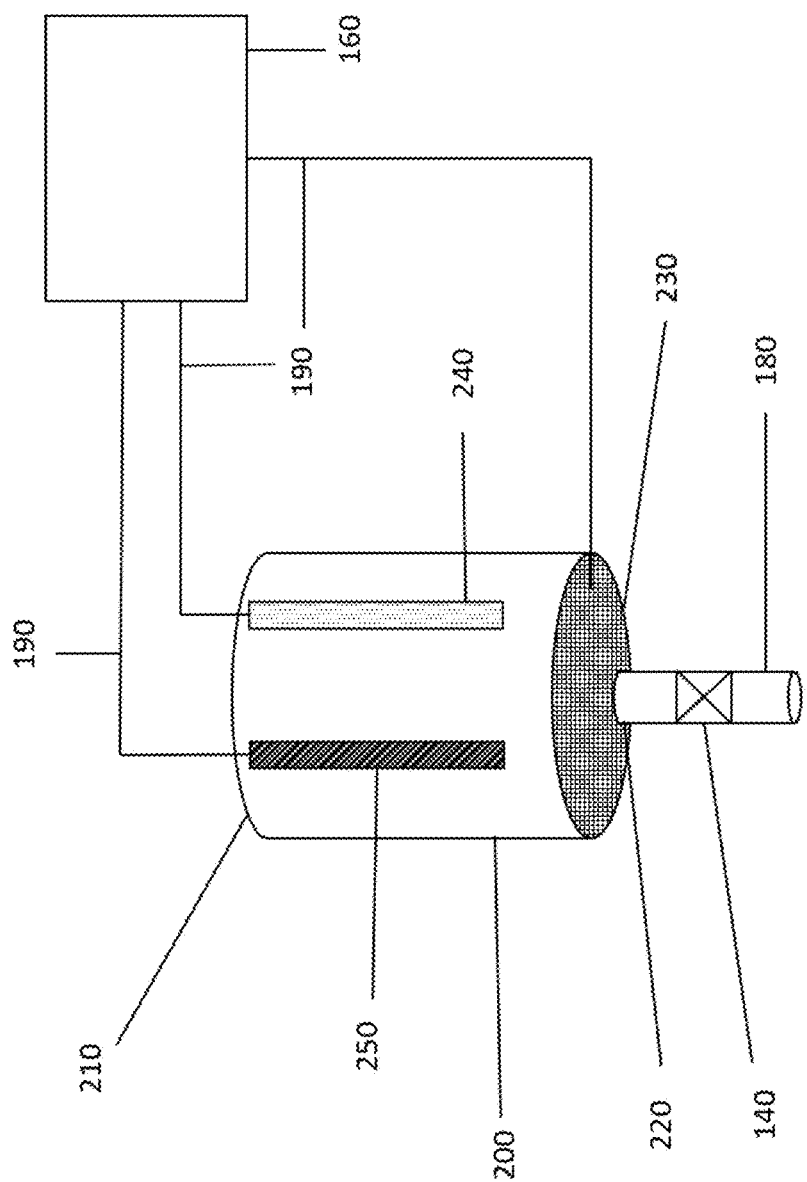
FIG. 2 shows the assay reaction chamber 200 in greater detail. The assay reaction chamber 200 contains an ingress opening 210 and an egress opening 220 through which a sample enters and exits the assay reaction chamber, respectively; three electrodes—a working electrode 230 (also called porous membrane) onto which are bound a plurality of analyte capturing molecules (not shown) that bind to the analyte being assayed, a counter electrode 240, and a reference electrode 250; and three connectors 190—one connector for each electrode that transmits information between the electrode and the potentiostat 160. Also shown in FIG. 2 is a pipe 180 and a flow control value 140 downstream of the egress opening 220.

As seen in FIG. 2, the assay reaction chamber 200 contains a working electrode (which is a porous membrane) 230 onto which is bound a plurality of analyte capturing molecules that binds to the analyte in the sample, a counter electrode 240, and a reference electrode 250. These electrodes are in electronic communication, via connectors 190, with the potentiostat 160, which, in turn, is electronic communication with the display 170 (not shown). The connectors 190 can be wires or other means of electronic communication. The assay reaction chamber 200 has two opening, an ingress opening 210 and an egress opening 220, through which the sample passes. A pipe 180 (not shown) is connected to the ingress opening 210 so that the sample can travel from the sample reservoir 110 into the assay reaction chamber 200. Another pipe 180 is connected to the assay reaction chamber's egress opening 220 and carries the sample to the waste reservoir 150 (not shown). A flow control valve 140 is located in the pipe 180 between the assay reaction chamber's egress opening 220 and the waste reservoir 150 (not shown). A working electrode 230 (which is porous and also referred to as a "porous membrane") spans the assay reaction chamber 200, forming a barrier between the ingress opening 210 and the egress opening 220 and through which the sample must traverse. The working electrode is a porous electron conductive material, and thus an electron transducer. In one embodiment, working electrode is a polymer containing graphite that percolates (e.g., graphite felt). In another embodiment, the porous membrane is a conductive polymer-carbon allotrope.

Shown in FIG. 2, the working electrode 230 is located on or near the bottom of the assay reaction chamber 200 surrounding the egress opening 220. In another embodiment, the working electrode can be located some distance from the bottom of the assay reaction chamber. In either embodiment, one may want to have a finite distance between the working electrode and the other two electrodes (counter electrode 240 and reference electrode 250) to prevent a short circuit from occurring. A counter electrode 240 and reference electrode 250 are screen-printed on the inside walls of the assay reaction chamber such that they are partially or fully submerged in the sample above the porous membrane and are separated by a finite distance from the working electrode. In one embodiment, an electrical lead (a connector 190) is screen-printed along the inside wall of the assay reaction chamber to serve as a means of electronic communication connection an electrode and the potentiostat 160. In an embodiment, the assay reaction chamber 200 contains one opening in its wall for each electrode present so that each electrode can be in electronic communication with the potentiostat via a connector 190. Each opening is filled with electronic fill material (not shown). In one embodiment, the electronic fill is a via fill. In one embodiment, the via fill material is a conductive epoxy. Conductive epoxies are not necessarily epoxy chemistry, but a thermoset plastic matrix that is filled with conductive particles, such as but not limited to, graphite, silver, copper, gold, and graphene. In one embodiment, a through via (Tech-Etch, Plymouth, MA) is used. In one embodiment, a bonding pad (not shown) is screen-printed over each electronic fill material on the outside of the assay reaction chamber. Each bonding pad is situated to be in electronic contact with a spring-loaded connector. The spring-loaded connector is in electronic communication with a potentiostat. In another embodiment, the flow-through electrochemical detection system has a different electrode pattern and with other electronic communication means for connecting to the potentiostat 160.

The assay reaction chamber can be disposable, that is, can be used once; or it can be reused for multiple assays. The analyte can be the same for multiple assays or can be different. In one embodiment, the flow-through electrochemical detection system, at a minimum, contains the assay reaction chamber with at least the porous working electrode to which analyte capturing molecules are bound and through which the sample traverses, the potentiostat, and the means for the assay reaction chamber to be in electronic communication with the potentiostat.

Prior to running a sample through the flow-through electrochemical detection system, the working electrode in the assay reaction chamber is pre-treated with an analyte capturing molecule so that, if the analyte is present in the sample, the analyte binds to the analyte capturing molecule. After the sample completely passes through the assay reaction chamber, one can optionally pass water or another substance through the flow-through electrochemical detection system or just the assay reaction chamber to wash out any substances that are not bound to the analyte capturing molecules. Then, an analyte detector is passed through the flow-through electrochemical detection system or just the assay reaction chamber. The analyte detectors bind to any analyte captured by the analyte capturing molecules. Optionally, one can optionally pass water or another substance through the flow-through electrochemical detection system or just the assay reaction chamber to wash out any unbound analyte detectors. In one embodiment, the analyte detector contains an enzyme or other compound which can generate a redox reaction when a chemical is added. A chemical is then added to the assay reaction chamber and, if the analyte is present, the analyte detectors generate a redox reaction. It is this redox reaction that generates an electric current across the porous membrane (working electrode) and which is detected and measured by the potentiostat (which is in electronic communication with the working electrode). The generated current can be visualized on the display and provides information about the quantity of the analyte present in the sample. If no analyte is present in the sample, nothing binds to the analyte capturing molecule, no analyte detector remains in the assay reaction chamber, and no current is generated by a chemical nor enzymatic reaction when the chemical or enzyme is applied to the assay reaction chamber.

Figure 4:
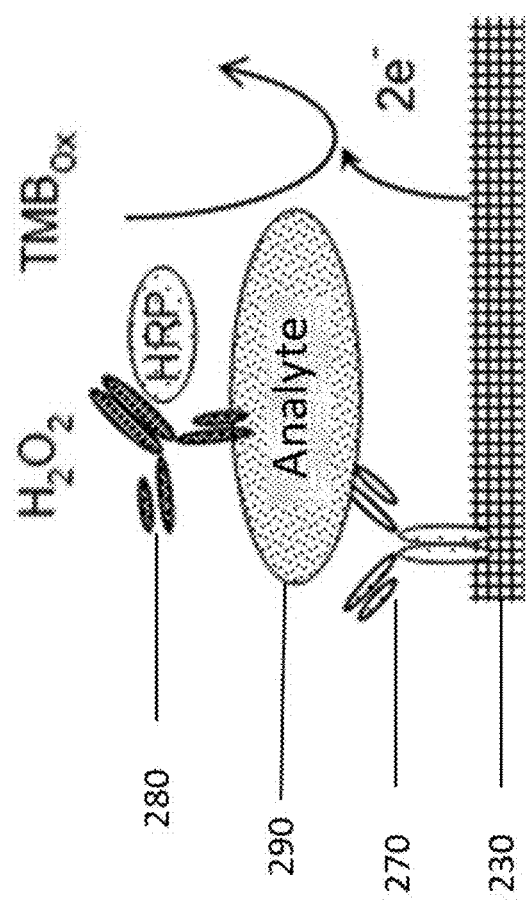
FIG. 4 depicts a two-site, noncompetitive immunoassay taking place at the surface of the working electrode 230. An analyte capturing molecule 270 (in this embodiment is shown as an antibody) is bound to the working electrode 230 and binds an analyte 290. Subsequently, one adds an analyte detector 280 (in this embodiment is shown as conjugated horseradish peroxidase (HRP)-labeled antibody) which binds to the analyte 290 and which facilitates the detection of that analyte through the oxidation of 3,3',5,5'-tetramethylbenzidine (TMB) in the presence of hydrogen peroxide ($H_2O_2$), thereby generating a current.

In the embodiment shown in FIG. 4, the analyte capturing molecules 270 are antibodies that are bound to the working electrode 230 and which bind to the analyte 290. The analyte detectors 280 are also antibodies that also bind to the analyte 290. The analyte detector antibodies can be the same or different antibodies as the analyte capturing molecule antibodies. The analyte detector can have an enzyme (horseradish peroxidase (HRP) is shown but other non-limiting examples include glucose oxidase, alkaline phosphatase, β-galactosidase, glucoamylase, urease, malate dehydrogenase, and glucose-6-phosphate dehydrogenase) conjugated to the antibody. In the shown embodiment, a chemical such as 3,3',5,5'-tetramethylbenzidine (TMB) (or any similar chemicals) reacts with HRP to generate an electric current. Examples of other chemicals that could be used are various phenols, ammonia, NAD+, glucose, ferrocene, alkaline phosphatase, 2-aminophenol, etc. In alternative embodiments, the analyte capturing molecules are viruses, bacteria, phages, nucleic acids, aptamers, proteins, etc., which are bound to the porous working electrode and are able to bind to the analyte as the analyte passes through the assay reaction chamber containing the porous working electrode Similarly, the analyte detector can be viruses, bacteria, phages, nucleic acids, aptamers, proteins, etc., that bind to the analyte and contains an enzyme or chemical that is used to generate electric current.

The porous working electrode has protrusions thereby increasing its surface area and thus sensitivity for detecting analytes. The porous working electrode has a conductivity ranging from approximately 10 (S/m) to approximately $10^7$ (S/m); a porosity ranging from approximately 25% to approximately 90%; and surface area to volume ratio ranging from approximately 0.25 $m^2/g$ to approximately 10 $m^2/g$.

The potentiostat determines the electron charge potential (or current) across the porous membrane, thus determining the amount of analyte (if any) is present in the sample. The potentiometer is in electronic communication with a display which indicates the current which can be compared to known current for known amounts of analyte and thereby enabling one to determine the amount of analyte present in the sample. The display contains a means for measuring the depth of a current peak and report both the position of the peak (mV) and the magnitude of the current (mA or μA). To determine the amount of analyte contained within a sample, a standard curve is generated by assessing the current signal for specific concentrations of analyte with multiple replicates to assess the standard deviation of the measurements. A positive control is used (can be supplied in a kit), and the value associated with the standard curve is recorded. Both the signals from the unknown sample and the positive control sample are used to mathematically assess the concentration of analyte in the unknown sample through interpolation. In an alternative embodiment, software is used to determine the analyte's quantity in the sample where the software compares potentiostat's output for the particular analyte to the pre-determined standard curves for that particular analyte.

Per the schematic in FIG. 1, the flow-through electrochemical detection system 100 can have a filter 130 upstream of the assay reaction chamber's 200 ingress opening. The sample being assayed passes through the filter prior to entering the assay reaction chamber to remove large particulate matter from the sample being assayed. Non-limiting examples of this filter include lava stone, pumice, zeolite, glass fibers, animal fibers (e.g., wool), synthetic fibers, and mesh. Non-limiting examples of synthetic fibers include polyvinylidene fluoride (PVDF), polyimide, poly(p-xylylene) (Paralyne™), and polyester. One of ordinary skilled in the art can use a sample's particle size distribution (PSD) to determine the geometry of the pores in the working electrode and/or the filter to accommodate suspensions with a particular size distribution of components in the mixture. If the sample contains a high quantity of particulate matter, one may want to remove some of that particulate matter prior to passing the sample through the flow-through electrochemical detection system. One of ordinary skill in the art is aware of various methods to remove the particulate matter from the sample without removing any (or remove minute quantities of) analyte from the sample. One well-known method involves passing the sample through a continuous flow through centrifuge.

As previously mentioned, the flow-through electrochemical detection system utilizes a chemical or enzymatic reaction in the assay reaction chamber to determine if an analyte is present in the sample being assayed. When the analyte is present, the chemical or enzymatic reaction generates an electric current which is detected by the working membrane. In one embodiment, the flow-through electrochemical detection system utilizes a modified ELISA to determine the amount of analyte in a sample. In this embodiment, the analyte capturing molecules and the analyte detectors are antibodies can bind to an analyte. In other embodiments, the analyte capturing molecules and/or the analyte detectors are DNA, RNA, aptamers, proteins/polypeptides, viruses, bacteria, and/or other agents that are capable of binding to the analyte. To be clear, one of ordinary skill in the art recognizes that the analyte capturing molecules and the analyte detectors do not have to be the same. For example, one can use an aptamer to capture the analyte and an antibody as the detectors. Further, the analyte capturing molecules are attached to the porous membrane/working electrode using known in the art techniques.

In one embodiment, the sample's flow-through rate can range between approximately 5 ml/hour to approximately 1000 ml/hour. In another embodiment, the sample's flow-through rate can range between approximately 0.0001 ml/hour and approximately 100 liters/hour. One of ordinary skill in the art recognizes that the working electrode's volume and the flow-through rate of the sample through the assay reaction chamber can vary independently of each other. Flow rate also is impacted by the sample's viscosity. One of ordinary skill in the art is able to determine the optimal volume and rate for a specific sample and analyte. In one embodiment, a working electrode having approximately 10 cc volume and a flow-through rate of approximately 5 ml/hour is a good starting point for determining the optimal conditions for a specific sample and analyte. One of ordinary skill in the art recognizes that the concentration and size of particulate matter in a sample will place constraints on the pore size, pore size distribution, and total porosity of the working electrode and one may need to filter the sample (as discussed above) or alter one or more of the working electrode's characteristics to control the sample's flow rate. When the working electrode is approximately 40% porous, then approximately 80% of the sample is contained within the porous membrane. When $\Sigma A_{pores} < A_{outlet}$ the flow rate will be dictated by the electrode (porosity, diameter, height), and when $\Sigma A_{pores} > A_{outlet}$ the flow rate is dictated by the area of the egress opening. In addition, the flow control valve 140 and/or the pump 120 can be adjusted to control the sample's flow-through rate. One of ordinary skill in the art can determine the optimal flow-through rate based on the user's needs.

The diameters of the assay reaction chamber's ingress opening 210 and egress opening 220 and the pipes 180, as well as the flow control valve 140 and the pump 120, can impact the height of the sample within the assay reaction chamber. In one embodiment, the diameter of the pipes throughout the system and the assay reaction chamber are constant and approximately the same size. In an alternative embodiment, the diameter of the pipes at various locations within the system may vary and the diameter of the assay reaction chamber's egress opening may differ from the diameter of the assay reaction chamber and/or its ingress opening.

In one embodiment, the assay reaction chamber's diameter can range from approximately 0.1 mm to approximately 500 mm. In another embodiment, the assay reaction chamber's diameter can range from approximately 5 mm to approximately 50 mm. In another embodiment, the assay reaction chamber's diameter can range between approximately 11 mm to approximately 30 mm. The diameter of the egress opening 220 can range from approximately 0.01 mm to approximately 100 mm, from approximately 0.1 mm to approximately 50 mm, from approximately 1 mm to approximately 5 mm, in various embodiments. In another embodiment, the egress opening's diameter is 3 mm. Egress opening with different sized diameters can be paired with the different electrode configurations. The size/volume of the working electrode can range from approximately 0.5 cubic centimeters to approximately 10 cubic centimeters in one embodiment. In alterative embodiments, the working electrode's volume can range from approximately 0.01 cc to approximately 100 cc. In one embodiment, the working electrode's diameter is the same as or slightly larger than the assay reaction chamber's egress opening's diameter so that the working electrode does not exit the assay reaction chamber into the pipe attached to the egress opening.

In one embodiment, the flow-through electrochemical detection system is operated at room temperature. In alternative embodiments, one of ordinary skill in the art recognizes that the system (or parts of the system) should be used at different temperatures, either higher or lower than room temperature. When using an enzyme (for example, horseradish peroxidase) to generate an electric current when the analyte is present, one of ordinary skill in the art recognizes that enzymatic activity generally doubles every 10° C. until the temperature reaches approximately 55° C. Thus, in some embodiments, one may add a heating element to the assay reaction chamber or utilize other well-known in the art methods to increase the temperature of the system or just the assay reaction chamber (especially after the analyte detector has attached to the analyte) to approximately 50° C. which would enhance the chemical or enzymatic reaction that generates the measured current. In an alternative embodiment, when one is using an oligonucleotides as the analyte capturing molecules and the analyte is also an oligonucleotide, one of ordinary skill in the art can determine the optimal temperatures for denaturing and annealing of DNA or RNA to the analyte capturing molecule. In addition, one would want to obtain the optimal temperature for performing PCR, if PCR is to be performed after the analyte is captured and is being used to amplify the oligonucleotides in order to determine the amount of analyte in the sample. Thus, in this embodiment, one of ordinary skill can determine these different temperatures, and heat and/or cool, as necessary using known in the art methods, the system and/or the assay reaction chamber to optimize the capture and detection of the analyte.

EXAMPLE 1

Graphite Felt Electrode to Glassy Carbon Electrode Sensitivity Comparison

Figure 3:
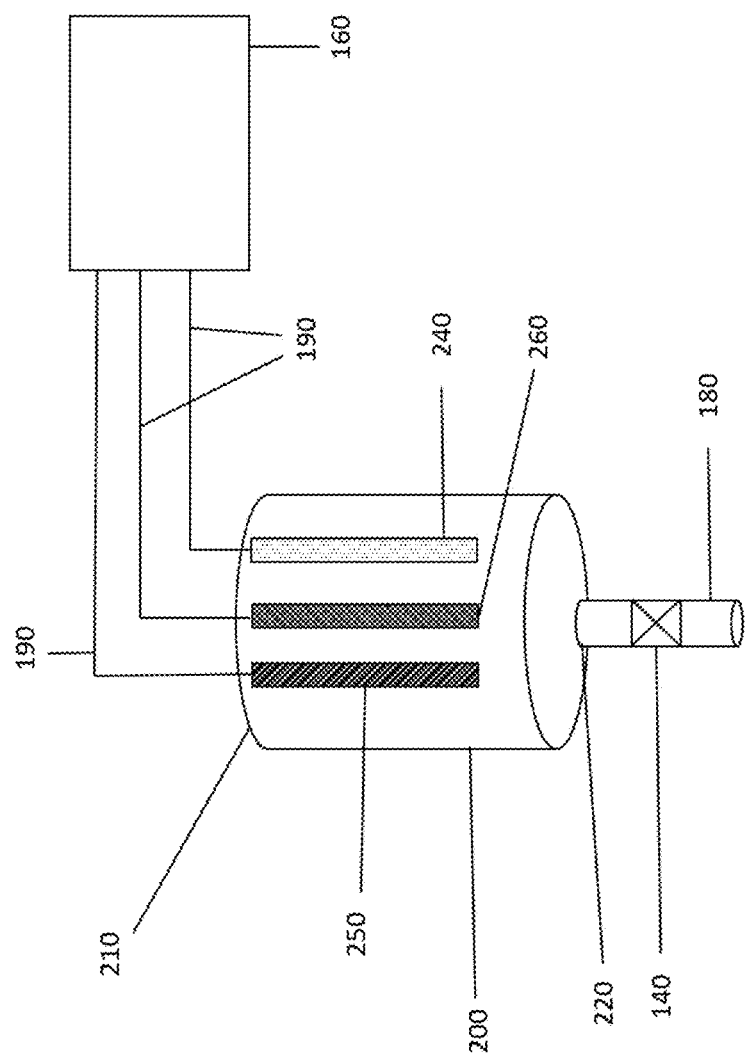
FIG. 3 shows a different embodiment of the assay reaction chamber 200.

The comparison of the detection sensitivity of an analyte using a graphite felt electrode (GFE, a porous working electrode) and a conventional glassy carbon electrode (non-porous) were performed. The response to identical enzymatic product concentrations was used to quantitatively compare the two electrodes. Because the enzymatic product can also be detected using optical transducers, colorimetric detection was employed to serve as a reference. Two 60 ml tubes were used as a model for the assay reaction chambers. As seen in FIG. 2, the assay reaction chamber 200, contained the GFE 230 (the working electrode) (Electrosynthesis, Lancaster, NY) at the assay reaction chamber's bottom, upstream of the flow control valve 140 and the assay reaction chamber egress opening 220. An Ag/AgCl reference electrode 250 (Bioanalytical Systems, Inc., West Lafayette, IN) and a platinum wire counter electrode 240 (VWR, Radnor, PA) were attached to the side of the assay reaction chamber. Each electrode was connected via wires 190 to the potentiostat 160 (BAS 100B/W electrochemical analyzer (Bioanalytical Systems, Inc., West Lafayette, IN) for electrochemical measurements. The parameters were set for Osteryoung Square Wave Voltammetry in a range of −1200 mV to 1200 mV with a sensitivity of 100 mA/V. As seen in FIG. 3, the second assay reaction chamber 200 contained a glassy carbon electrode 260 (Bioanalytical Systems, Inc., West Lafayette, IN) attached to the side of the assay reaction chamber. The glassy carbon electrode served as the working electrode. An Ag/AgCl reference electrode 250 (Bioanalytical Systems, Inc., West Lafayette, IN) and a platinum wire counter electrode 240 (VWR, Radnor, PA) were also attached to the side of the assay reaction chamber. The electrodes did not reach the assay reaction bottom, and were upstream of the flow control valve 140 and the assay reaction chamber egress opening 220. Each electrode was connected via wires 190 to the potentiostat 160 mentioned above using the same setting mentioned above. For both assay reaction chambers, the flow control valve 140 was closed so that the sample did not exit out the assay reaction chamber's egress opening.

A stock solution of 0.3 mM TMB was prepared by first adding 6 mg of TMB to 4 ml of acetonitrile. Note, 0.3 mM was determined to be the optimum concentration because lower concentrations produce weak signals, and concentrations exceeding 1.5 mM demonstrate precipitation of the enzymatic product which adversely affects the repeatability of the assay. The 0.3 mM TMB solution was then diluted with 75 ml of 0.20% sodium acetate buffer that contained 15 ml of acetonitrile and was titrated to a pH of 4.8-5.0 using acetic acid (approx. 100 µL) to generate the TMB stock solution. A fixed quantity (40 ml) of the TMB stock solution was taken, and 6.3 µL of 3% hydrogen peroxide was added per ml of the TMB stock solution to generate the TMB $H_2O_2$ solution. The TMB $H_2O_2$ solution is light sensitive and was kept in the dark prior to use. The stop solution was prepared by diluting concentrated sulfuric acid to 1M using Nanopure water.

Horseradish peroxidase (HRP) conjugated goat anti-*Salmonella* Common Structural Antigens-Plus antibodies (Ab) was purchased from SeraCare (Gaithersburg, MD). 10-fold serial dilutions of horse radish peroxidase conjugated antibody (Ab-HRP) in TMB substrate solution were prepared using antibody concentrations ranging from $2.67 \times 10^{-9}$ M to $2.67 \times 10^{-18}$ M. The total volume of each dilution was fixed at 10 ml with a final concentration of TMB and $H_2O_2$ in each dilution of 0.3 mM and 5.5 mM, respectively. Following an incubation period of 20 minutes in the dark at room temperature, 5 ml of stop solution was added each dilution. The Ab-HRP was removed from the solution using Centricon® centrifuge filters. 200 µL of solution was then transferred to a 96 plate well for absorbance measurements at $OD_{450}$. Colorimetric measurements were made using a Tecan Safire² plate reader (Männedorf, Switzerland) using an absorbance wavelength of 450 nm. The balance of the solution, 9.8 ml, was divided equally into the two assay reaction chambers described above for the electrochemical measurements. In summary, the enzymatic product was produced separately, then the enzyme was remove, and then the electrodes were used to detect the presence of the enzymatic product.

Figure 5:
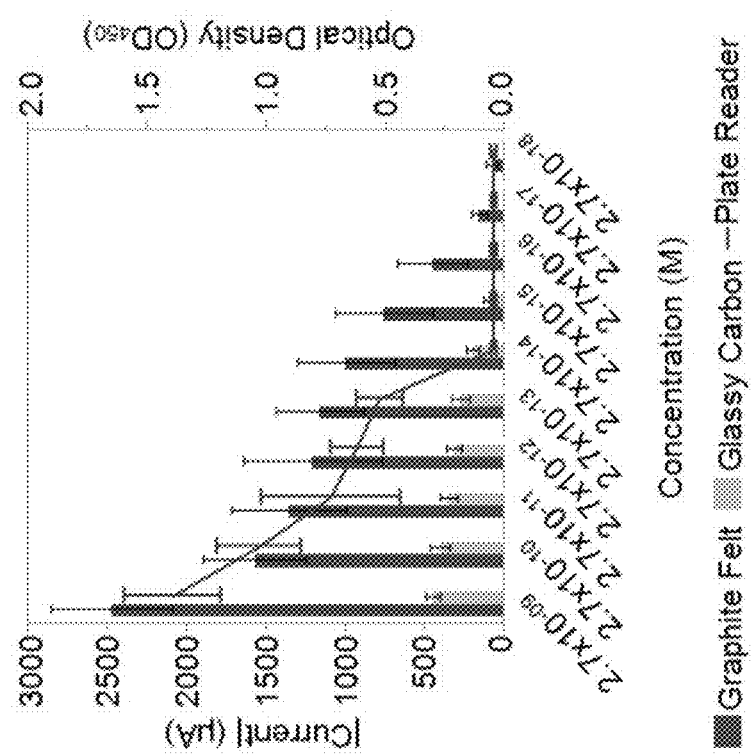
FIG. 5 illustrates that a graphite felt working electrode generates higher signal intensities which correlates to lower levels of detection compared to a glassy carbon working electrode. The effect of the electrode composition was determined by measuring the response of the graphite felt (gray bars) and glassy carbon (white bars) to the indicated concentrations of HRP-labeled antibodies containing TMB. The absolute value of the current (μA, y-axis on the left measured) at −340 mV for both the graphite felt and glassy carbon working electrodes are reported in addition to the optical density reading (black line) of the HRP-labeled antibody dilutions (y-axis on the right). Measurements represent the average values of three independent experiments with error bars indicating the standard error of the mean.

In FIG. 5, both the current and OD measurements demonstrate an apparent dose response associated with the conjugate's concentration. The limit of detection (LOD) for the glassy carbon electrode is $2.7 \times 10^{-15}$ M, which is fairly consistent with $8.5 \times 10^{-14}$ M (see, Volpe, et al., *Analyst.*, 123(6):1303-7 (1998)) and $2.2 \times 10^{-14}$ M (see, Fanjul-Bolado, et al., *Anal. Bioanal. Chem.*, 382(2):297-302 (2005)), reported values for carbon electrodes. Surprisingly and unexpectedly, the LOD for the graphite felt electrode was $2.7 \times 10^{-17}$ M, which was two logs more sensitive than the glassy carbon electrode. Not wishing to be bound to any particular hypothesis, the GFE's lower LOD might have resulted from one or more of the following: having a larger surface contact area, an improved ability to conduct an electrical charge, and/or a smaller diffusion distance compared to the glassy carbon electrode. In addition to its increased sensitivity, the graphite felt electrode is believed to be the superior material for the construction of a working electrode because it can be purchased at a much lower cost than the glassy carbon electrode.

EXAMPLE 2

Protein Detection

To assess the capability of the graphite felt to function as both a capture surface and working electrode, a pre-determined number of antibodies immobilized on the surface of the graphite felt was used to detect antibody-enzyme conjugate. Rabbit anti-goat IgG antibody (SeraCare, Gaithersburg, MD) was immobilized on the surface of the GFE followed by blocking with bovine serum albumin (BSA) from Sigma Aldrich (Billerica, MA Calculations were conducted with the intent of depositing 1 antibody for every 100 BSA proteins. To achieve this coating, 5 GFEs were first immersed in 5 mL of a $4.23 \times 10^{-8}$ M solution of rabbit anti-goat IgG, which was then flowed through the GFEs. The eluted solution was collected, reapplied to each respective GFE. The valve was closed and the electrode was allowed to incubate overnight. After 18-20 h, the GFE was rinsed twice with 5 mL PBST (0.5% Tween-20 in phosphate buffered solution (PBS)) and then exposed to 6 mL of 0.25 mg/mL of BSA in PBS. The BSA in PBS was flowed through the GFEs with the eluted solution being collected and then reapplied to each respective GFE. The BSA in PBS was then allowed to react for 30 min at room temperature. The GFEs were subsequently rinsed twice with 5 mL PBST. The positive control GFE was not immobilized with antibody, only BSA; and for the negative control, the rabbit anti-goat IgG was substituted with anti-*E. coli* O157:H7 antibody. The purpose of the negative control antibody is to deposit an antibody on the GFE's surface that will not recognize the protein (the Ab-HRP described below).

Horseradish peroxidase (HRP) conjugated goat anti-*Salmonella* Common Structural Antigens-Plus antibodies (Ab) was purchased from SeraCare (Gaithersburg, MD). 5 ml solutions of Ab-HRP were serially diluted from $2.7 \times 10^{-9}$ M to $2.7 \times 10^{-13}$ M. The Ab-HRP dilutions were flowed through the anti-*E. coli* O157:H7 and rabbit anti-goat antibody coated GFEs. The eluent was collected and then reapplied to each respective GFE and allowed to react for 60 min (with the valve closed) at room temperature. Following elution, the electrodes were rinsed twice with 5 mL PBST. Next, 5 mL of TMB $H_2O_2$ solution was applied to the GFEs and allowed to react for 20 min. Then 5 mL of the stop solution (1 M $H_2SO_4$) were added to the container and incubated for 5 min For the positive control, 0.5 mL of $2.7 \times 10^{-9}$ M Ab-HRP containing 5 mL of 0.3 mM TMB and 32 μL of 5.5 mM $H_2O_2$ was applied, incubated for 20 min, and then processed with stop solution. The counter and references electrodes are suspended from the top of the container in a manner which ensures they are submerged in the solution and are 15 mm above the GFE (FIG. 2). The electrodes are connected to the potentiostat before the electrochemical measurements were obtained and recorded.

Figure 6:
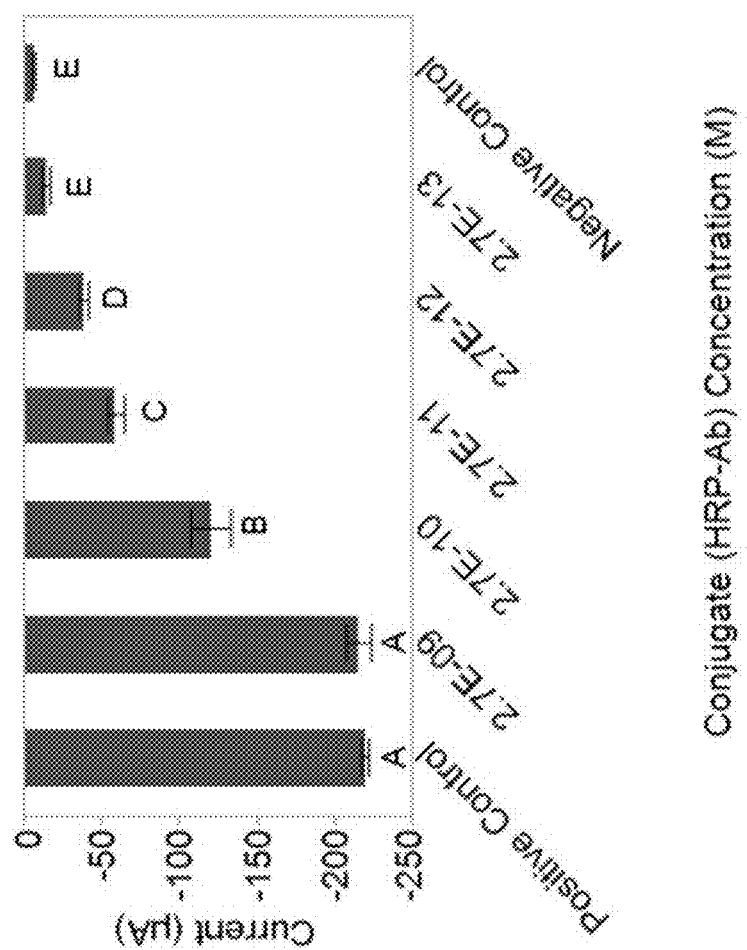
FIG. 6 shows the current (μA) generated by a fixed concentration of analyte capturing molecules (in this example, rabbit anti-goat antibody) and various concentrations ($10^{-9}$ to $10^{-13}$) of the analyte detector (in this example, HRP-labeled goat anti-Salmonella Ab) in an assay reaction chamber containing a graphite felt working electrode to which the analyte capturing molecules are bound. The bars represent the average current response generated for four trials with the error bars representing one standard deviation of the mean. Significance between measured electric current signals is noted by different letters as determined by a Student's t-test at a 95% confidence level.

The current responses for each level of conjugate antibody concentration are presented in FIG. 6. From the dose dependent response, the rabbit anti-goat antibodies immobilized appeared to have captured the goat antibodies specific for *Salmonella* that were conjugated to HRP, while the anti-*E. coli* antibodies did not capture the conjugate. The values of the current responses were compared using Student's t test with α=0.05. The Student's t cannot differentiate the positive control from $2.7 \times 10^{-9}$M nor can the negative control be differentiated from $2.7 \times 10^{-13}$M. However, the individual Student's t tests indicate that the data generated for each concentration was statistically different from one another for every 10-fold dilution. Based on these data, the GFE working electrode in the assay reaction chamber has a dynamic range of 5 orders of magnitude and displays sufficient resolution to provide a quantitative response. From the individual t-tests, the smallest discernable concentration of conjugate antibody that was statistically different from the negative control was $2.7 \times 10^{-12}$ M.

EXAMPLE 3

*Salmonella enterica* Serovar Typhimurium Detection

Affinity purified goat anti-*Salmonella* Common Structural Antigens IgG antibodies (Gaithersburg, MD) were immobilized on the surface of 0.25 inch thick GFE (Electrosynthesis, Lancaster, NY). Two experimental conditions were evaluated: 1 antibody for every 100 blocking proteins (BSA) and 1 antibody for every 10 blocking proteins (BSA). To achieve a coating of 1:100, 6 GFEs in assay reaction chambers were first immersed in 5 ml of $4.23 \times 10^{-8}$ M solution of goat anti-*Salmonella* IgG and then the solution was gravity flowed through the GFEs. The eluent was collected, reapplied to each respective GFE, and allowed to incubate overnight. This procedure was repeated for a negative control GFE where the goat anti-*Salmonella* IgG was substituted with goat anti-*E. coli* O157:H7. This same process was repeated for the 1:10 coating, however the concentration of goat anti-*Salmonella* antibody was increased to $4.23 \times 10^{-7}$ M. Following 18-20 hours, the GFE was rinsed twice with 5 ml PBST, and then exposed to 15 ml 0.25 mg/ml of nonfat powdered milk. The BSA containing blocking solution was then flowed through the different GFEs, with the eluent being collected and then reapplied to each respective GFE. After 30 minutes incubation at room temperature in the BSA containing blocking solution, GFEs were subsequently rinsed twice with 5 ml PBST. The positive control was not immobilized with antibody, as only BSA containing blocking agent was applied to the GFE.

10-fold serial dilutions of heat-killed *Salmonella* were generated to ensure that 500 to $5 \times 10^7$ cells were suspended in 5 ml and 60 ml solutions of PBS. These cell solutions were flowed through the GFEs in the assay reaction chambers, with the eluted heat-killed *Salmonella* solution being subsequently returned to the vessel containing the GFE and incubated for 1 hour. Following 1 hour incubation, the heat-killed *Salmonella* solution was flowed through the GFEs and the GFEs were twice rinsed with 5 ml of PBST.

Horseradish peroxidase (HRP) conjugated goat anti-*Salmonella* Common Structural Antigens-Plus antibodies (Ab) was purchased from SeraCare (Gaithersburg, MD). 5 ml Ab-HRP solutions of $2.7 \times 10^{-9}$ M Ab-HRP were flowed through the anti-*E. coli* O157:H7 and anti-*Salmonella* coated GFEs. The eluent was collected and then reapplied to each respective GFE and incubated at room temperature for 1 hour. Following elution, the GFEs were rinsed twice with 5 ml PBST. Next, 5 ml of TMB $H_2O_2$ solution was applied to the GFEs in the assay reaction chamber and allowed to react for 20 minutes in the dark. After 20 minutes, 5 ml of the stop solution (1 M $H_2SO_4$) was added to the assay reaction chamber. The working electrode, reference electrode, and counter electrodes were in electronic communication with the potentiostat via wires. Five minutes following the addition of the stop solution, the electrochemical measurements were recorded using a BAS 100B/W electrochemical analyzer (Bioanalytical Systems, Inc., West Lafayette, IN). The parameters were set for Osteryoung Square Wave Voltammetry in a range of −1200 mV to 1200 mV with a sensitivity of 100 mA/V, as discussed above.

Horseradish peroxidase (HRP) conjugated goat anti-*Salmonella* Common Structural Antigens-Plus antibodies (Ab) was purchased from SeraCare (Gaithersburg, MD). 0.5 ml of $2.7 \times 10^{-9}$ M Ab-HRP in 5 ml of TMB $H_2O_2$ were applied to the positive control. The solution was incubated for 20 minutes in the dark, and then 5.5 ml of the stop solution was added. Five minutes following the addition of the stop solution, the electrochemical measurement was performed as described above.

Figure 7:
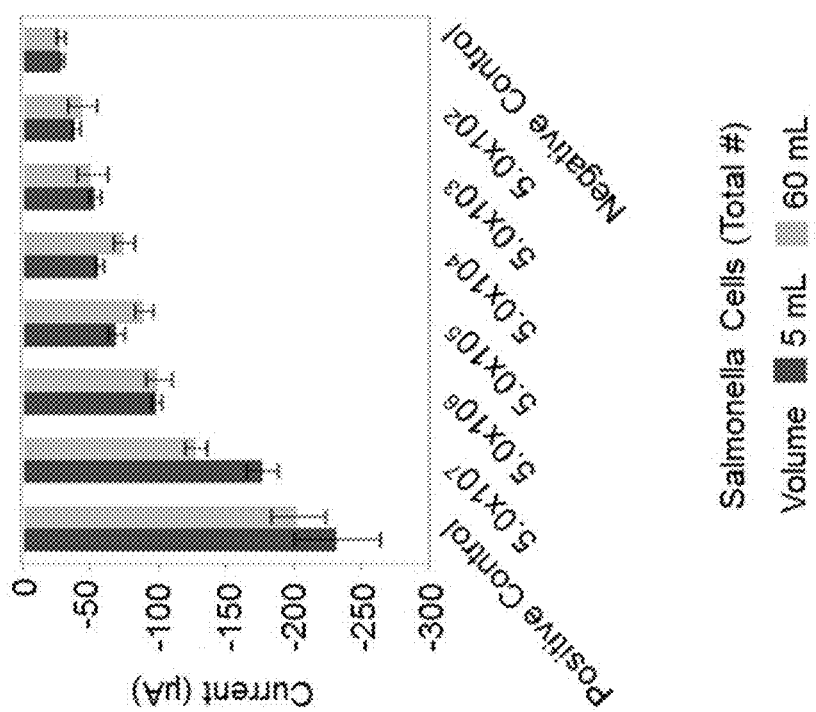
FIG. 7 shows, at −340 mV, the current generated by the working electrode when S. enterica serovar Typhimurium at concentrations ranging from $10^2$ to $10^7$ are passed through the assay reaction chamber containing analyte capturing molecules (in this example, goat anti-Salmonella Ab) bound to the GFE working electrode in either 5 ml (dark bars) or 60 ml (lighter bars) of fluid and after which the analyte detector (in this example, HRP-labeled goat anti-Salmonella Ab with TMB and $H_2O_2$) is passed through the assay reaction chamber. Measurements represent the average values of three independent experiments with error bars indicating the standard error of the mean.

As seen in FIG. 7, two different suspension volumes (5 and 60 ml) containing an identical number (ranging from $10^2$ to $10^7$) of heat inactivated *S. enterica* serovar *Typhimurium* generated a dose-dependent response which correlated to the number of heat inactivated *Salmonella* cells in the test suspension, and that the response appeared to be independent of sample volume. The current at −340 mV was measured. Darker bars represent 5 ml sample; lighter bars represent 60 ml solution. Measurements represent the average values of three independent experiments with error bars indicating the standard error of the mean.

However, upon closer examination of the data, it becomes apparent that there was a larger spread in the 60 ml sample data. When the data was analyzed in the same manner as the 5 ml sample, the lowest signal that could be statistically differentiated from the negative control was 50,000 (p=0.002). The larger spread in the data for the 60 mL samples prevent the 5,000 *Salmonella* cell sample from being statistically different from the negative control (p=0.0789), thus making the limit of detection higher when the larger volume of liquid was used. In comparison, when the signal for 5,000 *Salmonella* cells was compared to the negative control, the p value is 0.0789.

EXAMPLE 4

Effect of Flow-Rate on Pathogen Detection

To evaluate the effect of flow rate on the sensor response, 3 conditions were assessed using a 5 mL sample. The first condition was a static incubation of the sample (no fluid flow) for 1 h, which was used in the previous trials for *Salmonella*. The other two conditions assessed a direct flow of the sample through the sensor, at slow (0.1 mL/min) and fast (16.66 mL/min) rates. Using the above described protocol for detecting heat-inactivated *S. enterica* serovar Typhimirium with the flow-through electrochemical detection system, heat-inactivated *Escherichia coli* O157:H7 were added to 5 ml samples at concentrations ranging from $10^2$ to $10^7$ and passed through the flow-through electrochemical detection system as described above. The analyte capturing molecule was BacTrace goat anti-*E. coli* O157:H7 antibody SeraCare (Gaithersburg, MD) and was attached to the working electrode as described above. After passing each sample through the assay reaction chamber, the analyte detector, 5 ml of $2.7 \times 10^{-9}$ M BacTrace anti-*Escherichia coli* O157:H7 antibody, peroxidase-labeled was flowed through the sample treated GFEs. The eluent was collected and then reapplied to each respective GFE and allowed to react for 60 min (with the valve closed) at room temperature. Following elution, the electrodes were rinsed twice with 5 mL PBST. Next, 5 mL of TMB $H_2O_2$ solution was applied to the GFEs and allowed to react for 20 min in the dark. Then 5 mL of the stop solution (1 M $H_2SO_4$) were added to the container and incubated for 5 min; The results of this experiment are presented in FIG. 8.

Figure 8:
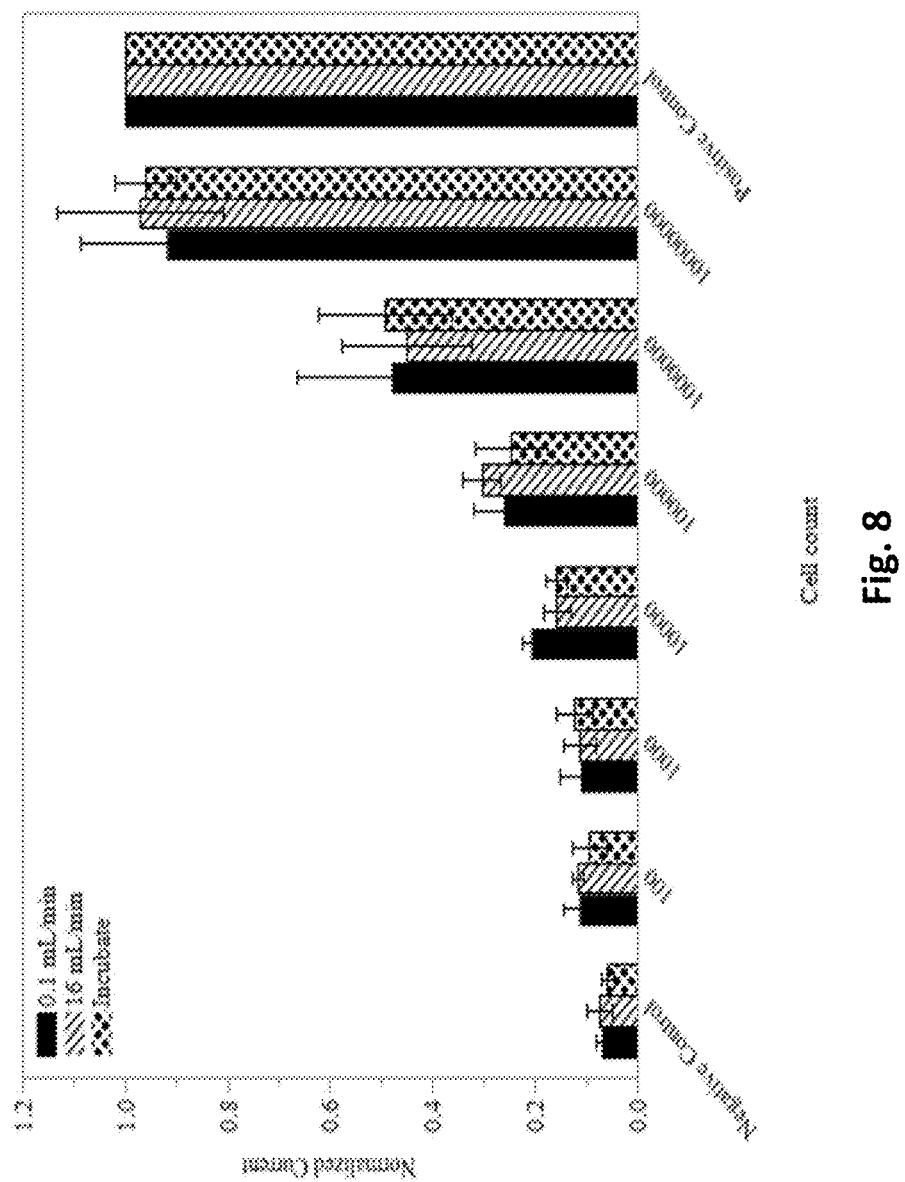
FIG. 8 shows the normalized current response was measured upon exposing the sensor to E. coli O157:H7 cells ($10^2$-$10^7$ CFU) in a 5 mL sample volume using static (solid bars), slow (dashed bars) or fast (dot bars) sample flow conditions. The average response from three independent trials is plotted with the error bars representing the standard deviation from the mean.

FIG. 8 also shows the normalized current response was measured upon exposing the sensor to *E. coli* O157:H7 cells ($10^2$-$10^7$ CFU) in a 5 mL sample volume using static (dot bars), slow (solid bars) or fast (dashed bars) sample flow conditions. The average response from three independent trials is plotted with the error bars representing the standard deviation from the mean.

A cursory examination of the data indicates that the average response of the sensor was similar for static incubation and flow-through conditions. Upon closer inspection it was clear that there was a higher variation between trials under the flow-through conditions compared to the static incubation for 1 hr. The Individual Student's t-test ($\alpha=0.05$) were conducted to compare the dose dependent response generated for the different flow rates. The tests indicate that there was no significant difference between the normalized current responses.

Student's t-tests were conducted to compare the normalized responses for the negative control and the different number of cells present in the sample. The limit of detection for *E. coli* cells in 5 mL of PBS buffer is 1000 cells for static incubation, p=0.043. These results are consistent with previous experiments that used similar conditions to detect *Salmonella*. The limit of detection for both of the flow conditions was determined to be equal to 10,000 cells in 5 mL; p=0.0468 for 0.1 mL/min, p=0.0104 for 16.66 mL/min.

EXAMPLE 5

Detection Using Different Sample Volumes

Figure 9:
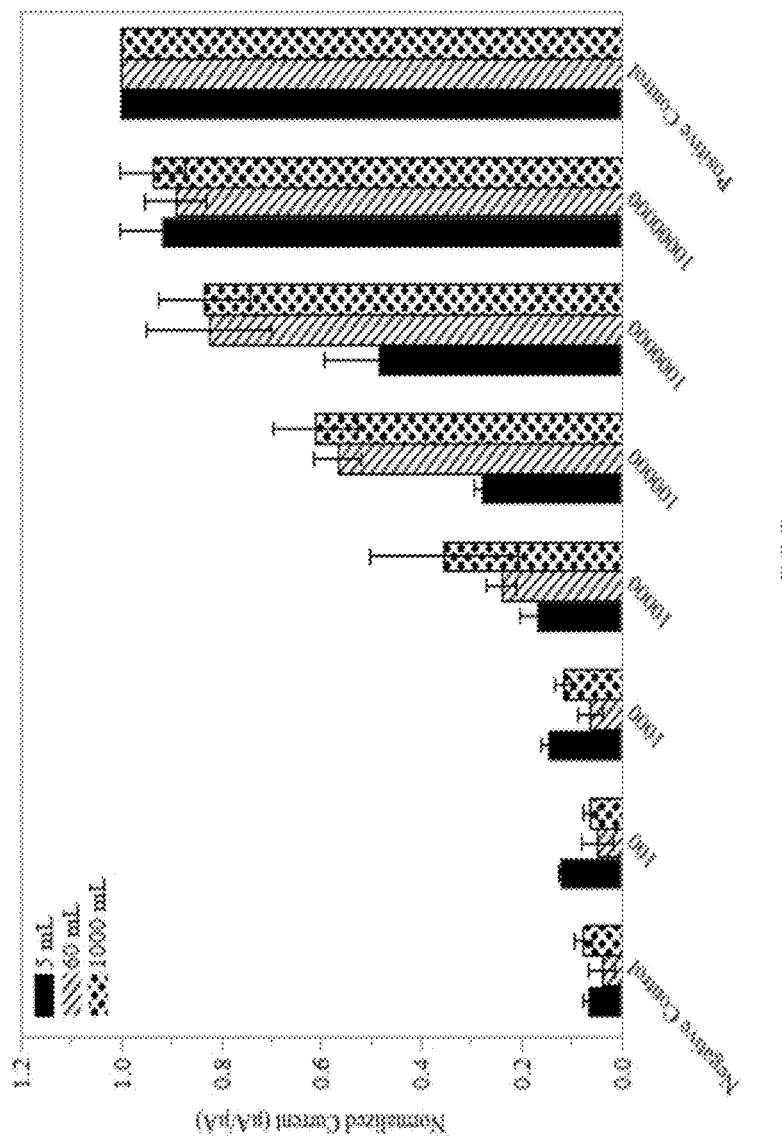
FIG. 9 shows mL (dashed bars) and 1000 mL (dot bars) through the GFE at a rate of 16.66 mL/min. The average normalized current values for three trials is reported with error bars denoting 1 standard deviation from shows a normalized current response generated upon flowing a suspension of E. coli O157:H7 in PBS with cell numbers ranging from 102-107 CFU in sample volumes of 5 mL (solid bars) 60 the mean.

A similar protocol to the one described in Example 5, was used to assess the impact of sample volume on the sensor responses. FIG. 9 displays the results of three independent trials of *E. coli* detection using 3 different sample volumes at a fixed flow rate. The rate of flow was targeted to be 16.66 mL/min to ensure that the 1 L sample would be passed through the device within 1 hr. Note, as the valve used in the experimental set-up was analog and manually actuated, the variation in time to complete flow-through varied by ±1 minute. Thus, the duration of the exposure for the 5 mL, 60 mL and 1000 mL samples were less than 1 min, less than 4 min, and was less than one hr., respectively.

FIG. 9 shows 60 mL (dashed bars) and 1000 mL (dot bars) through the GFE at a rate of 16.66 mL/min. The average normalized current values for three trials is reported with error bars denoting 1 standard deviation from shows a normalized current response generated upon flowing a suspension of *E. coli* O157:H7 in PBS with cell numbers ranging from $10^2$-$10^7$ CFU in sample volumes of 5 mL (solid bars) 60 the mean.

As with the sensor response using different flow rates, there does not appear to be a significant impact on the sensor performance when different volumes are used. The response for the 5 mL volume is the lowest. Even though it has the highest concentration (total cell counts were equivalent for the different volumes), the flow-through rate was the fastest. As observed in FIG. 10, the flow rate can affect the sensor response and compared to static incubation the limit of detection can be affected.

While the normalized current measured for the different sample volumes varied, the limit of detection for each volume was not affected. Student's t-tests were conducted to compare the normalized responses for the negative control and the different number of cells present in the sample. The limit of detection for *E. coli* cells in PBS buffer is 10,000 cells for 5 mL, p=0.029, 10,000 cells for 60 mL, p=0.004, and 10,000 cells for 1000 mL, p=0.003.

EXAMPLE 6

*Escherichia coli* Detection in Water and Liquefied Food

Figure 10:
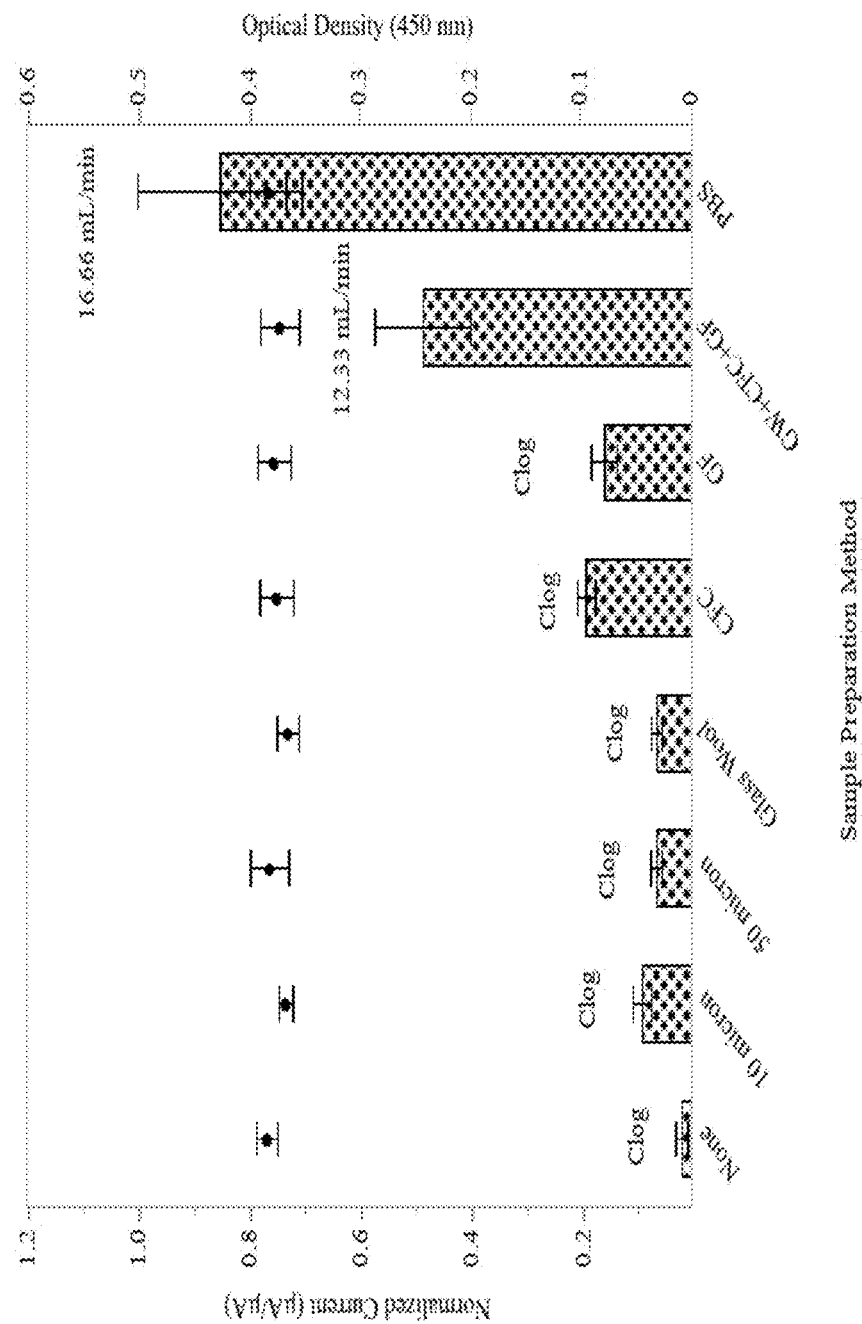
FIG. 10 shows flow rates and signals generated from a positive control were evaluated both via the electrochemical sensor (bars and left-hand y axis) and optically (points and right-hand y axis) to decipher the impact of different sample preparation methods on flow rate and signal intensity. 10 micron filters, 50 micron filters, glass wool (GW), graphite felt (GF), and continuous flow centrifugation (CFC) were first performed individually, then the GW, CFC, and GF were used tandemly as methods for clarification of ground beef samples. PBS was used as a control and thus, did not contain ground beef homogenate.

Preliminary trials performed with ground beef suggested that food products could clog the GFE and reduce the detected signal amplitude. In an effort to circumvent these issues, samples were subjected to filtration via glass wool, and graphite felt in addition to continuous flow centrifugation (CFC). These methods were chosen for their particle size distribution patterns and the resulting compositional analysis obtained post processing as reported previously with lean ground beef. The flow rate and the signal generated from a positive control were evaluated both electrochemically as well as optically to decipher the impact of the sample preparation on flow rate and signal intensity (FIG. 10). From this, it was determined that proper sample pre-treatment can prevent the filter from becoming clogged. It also indicated that something in the food matrix appears to affect the ability to detect the signal electrochemically because the signal intensities varied with the use of different sample preparation techniques and matrices when measured using electrochemically yet no significant difference is seen between the signals when measured via optical density. Taken together, this indicates that the product is being formed by the enzyme substrate reaction in the presence of the meat in a manner that is similar to that of buffer.

FIG. 10 shows flow rates and signals generated from a positive control were evaluated both via the electrochemical sensor (bars and left-hand y axis) and optically (points and right-hand y axis) to decipher the impact of different sample preparation methods on flow rate and signal intensity. 10 micron filters, 50 micron filters, glass wool (GW), graphite felt (GF), and continuous flow centrifugation (CFC) were first performed individually, then the GW, CFC, and GF were used tandemly as methods for clarification of ground beef samples. PBS was used as a control and thus, did not contain ground beef homogenate.

It is likely that the removal of the large sized particulate matter could help facilitate the flow of sample through the pores of the GFE. However, the GFE still appeared to clog during the course of flowing 1 L of buffer containing 325 g of beef homogenate through the sensor even after any of the individual pretreatments were performed. Through trial and error an effective pretreatment that included the use of glass wool, continuous flow-through centrifugation, and graphite felt in tandem was found to allow the entire sample to flow-through the sensor and enable the detection of an electrochemical response. Though buffer samples were able to obtain flow rates of 16 mL/min, the fastest speed obtained with ground beef homogenates was 12.33 mL/minute after significant pretreatment of the sample. This is probably due to the collection of smaller particles within the pores of the filter, which ultimately restricts the flow rate through the system.

Figure 11:
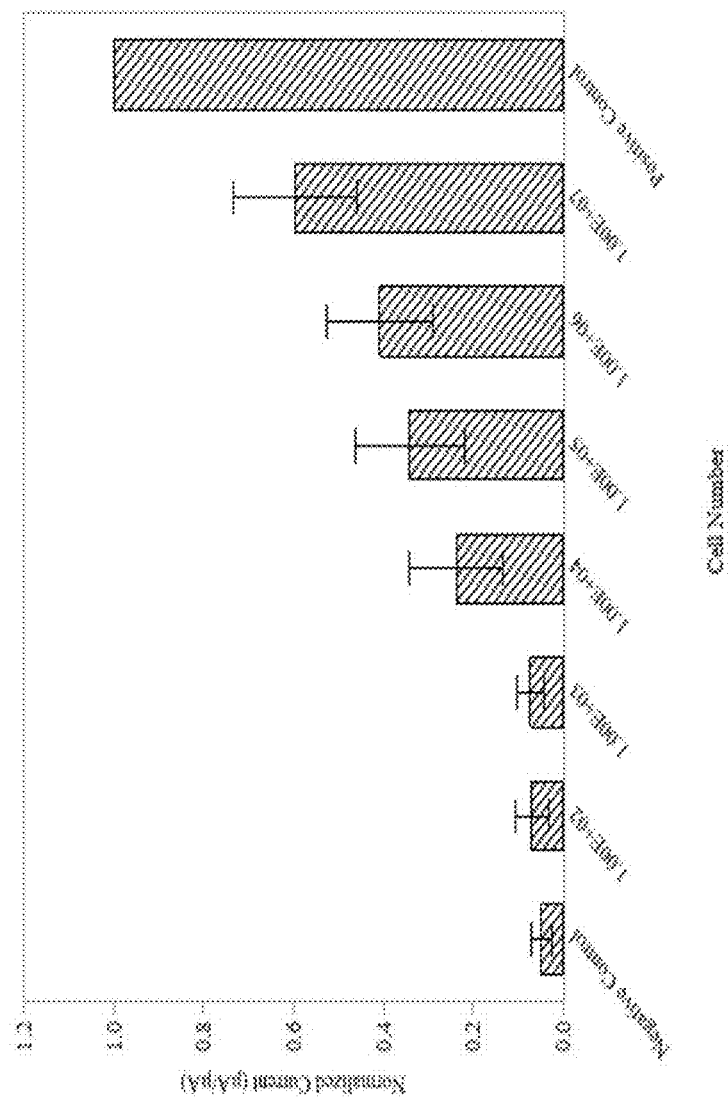
FIG. 11 shows a sensor response to pretreated ground beef homogenate, inoculated with a fixed number of E. coli O157:H7 cells. Ground beef homogenates inoculated with $10^2$-$10^7$ live E. coli cells were pretreated using the GW, CFC, and GF in tandem before being flowed through the graphite felt electrochemical sensor and the resulting currents, normalized to the positive control, were recorded.

Following the demonstration that the sensor could detect *E. coli* in different sample volumes in a flow-through assay, and that a complex background matrix, such as ground beef homogenate would not clog or adversely affect the response of the electrochemical assay with proper pretreatment of the sample, detection of *E. coli* within ground beef homogenate was conducted. FIG. 11 demonstrates the average dose response of 3 independent trials, where the normalized current is presented on the y-axis and the total number of cells in the treated sample is depicted on the x-axis. The error bars in this graph denote the standard deviation of the mean.

FIG. 11 shows a sensor response to pretreated ground beef homogenate, inoculated with a fixed number of *E. coli* O157:H7 cells. Ground beef homogenates inoculated with $10^2$-$10^7$ live *E. coli* cells were pretreated using the GW, CFC, and GF in tandem before being flowed through the graphite felt electrochemical sensor and the resulting currents, normalized to the positive control, were recorded.

Student's t-tests were conducted to compare the normalized responses for the negative control and the different number of cells present in the sample to determine the limit of detection. The limit of detection was determined to be 100,000 cells, p=0.035.

EXAMPLE 7

Oligonucleotide Detection

In one embodiment, the analyte capturing molecule bound to the porous working electrode can be an oligonucleotide that captures a complementary polynucleotide sequence within the sample. The analyte detector is a second oligonucleotide, which contains a modified nucleotide (such as biotin-dT), enzyme (such as a HRP-oligo probe), or similar entity for detection purposes. In such an embodiment, antibiotin antibodies conjugated with HRP may be necessary to provide the enzyme for the reaction that generates the electric current.

Using a protocol similar to antibody immobilization discussed in prior examples a biotin binding protein was immobilized on the surface of the graphite felt. Specifically, a $6.25 \times 10^{-7}$ M solution of neutralavadin protein (Thermo Fisher Scientific) was prepared and then flowed through the GFEs. The eluted solution was collected, reapplied to each respective GFE. The valve was closed and the electrode was allowed to incubate overnight. After 18-20 h, the GFE was rinsed twice with 5 mL PBST (0.5% Tween-20 in phosphate buffered solution (PBS)) and then exposed to 6 mL of 0.25 mg/mL of BSA in PBS. The BSA in PBS was flowed through the GFEs with the eluted solution being collected and then reapplied to each respective GFE. The BSA in PBS was then allowed to react for 30 min at room temperature. The GFEs were subsequently rinsed twice with 5 mL PBST. Next, 5 mL of a $2 \times 10^{-4}$ M solution of biotinylated oligo was applied to each GFE, and allowed to statically incubate at room temperature for 2 hours. The GFEs were subsequently rinsed twice with 5 mL PBST. Data generated for antibody labeled HRP was used as a reference to design the conjugate with the intent of retaining number of HRP molecules a constant. Specifically, 5 ml solutions of a complimentary oligo conjugated with HRP (1:1) were serially diluted from $1.3 \times 10^{-10}$ M to $2.7 \times 10^{-15}$ M. The oligo-HRP dilutions were flowed through the GFEs and the eluent was collected and then reapplied to each respective GFE and allowed to react for 60 min (with the valve closed) at room temperature.

Following elution, the electrodes were rinsed twice with 5 mL PBST. Next, 5 mL of TMB $H_2O_2$ solution was applied to the GFEs and allowed to react for 20 min. Then 5 mL of the stop solution (1 M $H_2SO_4$) were added to the container and incubated for 5 min. 200 μL of solution was then transferred to a 96 plate well for absorbance measurements at $OD_{450}$. Colorimetric measurements were made using a Tecan Safire$^2$ plate reader (Männedorf, Switzerland) using an absorbance wavelength of 450 nm. The counter and references electrodes are suspended from the top of the container in a manner which ensures they are submerged in the solution and are 15 mm above the GFE (FIG. 2). The electrodes are connected to the potentiostat before the electrochemical measurements were obtained and recorded. The current responses and absorbance for each level of olig-HRP conjugate are presented in FIG. 12. The graph shows a dose dependent response for both absorbance and measured current. The lower limit of detection for electrochemical detection appears to be $1.3 \times 10^{-13}$ M and one order of magnitude higher, $1.3 \times 10^{-12}$ M for detection using absorbance.

Figure 12:
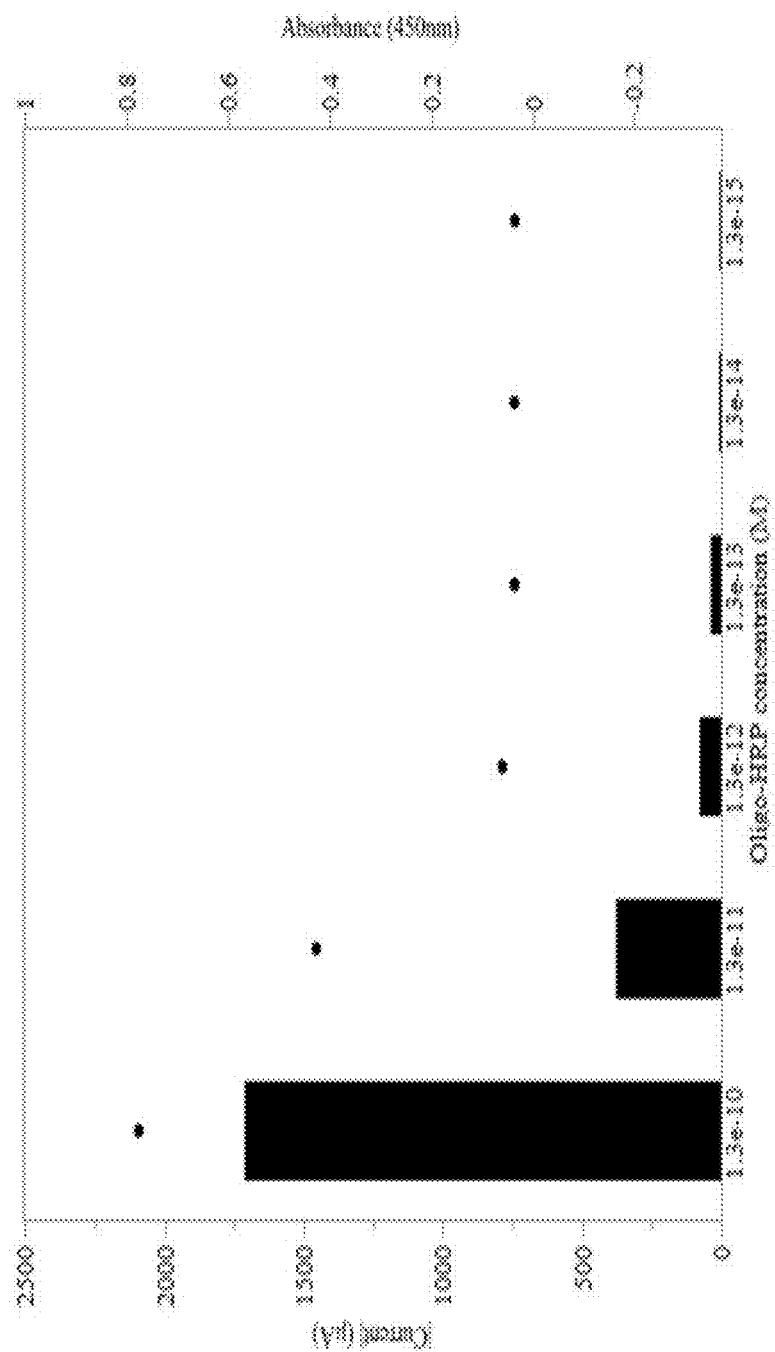
FIG. 12 shows the detection of complimentary oligo fragments.

FIG. 12 shows a detection of complimentary oligo fragments. FIG. 12 graphically depicts the concentration of oligo-HRP that is complimentary to the oligo immobilized on the GFE. The electrochemical responses are represented by black bars (current in μAmps left y-axis) and the absorbance measurements are depicted as pints (absorbance @450 nm, right y-axis).

Calculated temperatures (higher than ambient temperature) may also be necessary to provide increased specificity during the complementary sequence capture and can be supplied through the use of a temperature-controlled chamber or heating element around the assay reaction chamber.

EXAMPLE 8

Detection of *Salmonella* and *E. coli*

Figure 13:
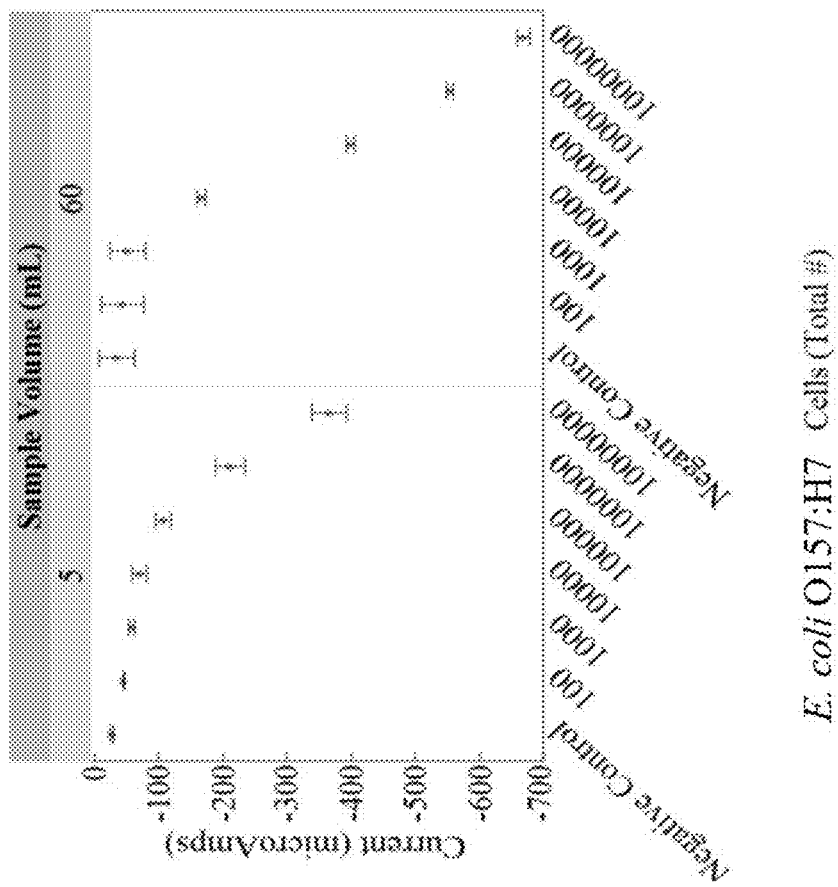
FIG. 13 graphically depicts the concentration of oligo-HRP that is complimentary to the oligo immobilized on the GFE. The electrochemical responses are represented by black bars (current in μAmps left y-axis) and the absorbance measurements are depicted as pints (absorbance @450 nm, right y-axis).

Using the above described protocol for detecting heat-inactivated *S. enterica* serovar Typhimirium with the flow-through electrochemical detection system, heat-inactivated *Escherichia coli* O157:H7 were added to 5 ml and 60 ml samples at concentrations ranging from $10^2$ to $10^7$ and passed through the flow-through electrochemical detection system as described above. The analyte capturing molecule was BacTrace goat anti-*E. coli* O157:H7 antibody SeraCare (Gaithersburg, MD) and was attached to the working electrode as described above. After passing each sample through the assay reaction chamber, the analyte detector, 5 ml of $2.7 \times 10^{-9}$ M BacTrace anti-*Escherichia coli* O157:H7 antibody, peroxidase-labeled was flowed through the sample treated GFEs. The eluent was collected and then reapplied to each respective GFE and allowed to react for 60 min (with the valve closed) at room temperature. Following elution, the electrodes were rinsed twice with 5 mL PBST. Next, 5 mL of TMB $H_2O_2$ solution was applied to the GFEs and allowed to react for 20 min in the dark. Then 5 mL of the stop solution (1 M $H_2SO_4$) were added to the container and incubated for 5 min; FIG. 13 shows the current (μA) for each concentration of *E. coli* O157:H7. As seen in FIG. 13, the signal generated for *E. coli* O157:H7 can be 2-5× larger than those recorded for *S. enterica* serovar Typhimirium, using identical test conditions. However, while the signals are larger for *E. coli*, the limit of detection remains similar; approximately 10,000 cells in either 5 mL or 60 mL.

To demonstrate that the flow-through electrochemical detection system detects *E. coli* O157:H7 in a food sample, one loop of *E. coli* was taken from a frozen culture and inoculated 25 ml of Luria-Bertani (LB) broth. The culture was grown overnight at 37° C. with shaking at 160 rpm. Cell concentration was quantified using 6×6 drop technique (see, Chen, et al., *J. Microbiol. Methods* 55(2):475-9 (2003)). 600 μl of a $10^9$ *E. coli* overnight culture was used to inoculate 25 g of ground beef in 75 mL of growth media, and hand massaged to homogenize the sample. No enrichment was utilized, and the samples were processed immediately (i.e., homogenized using a blender).

Prior to flowing the ground beef homogenate through the assay reaction chamber containing the GFE working electrode, the ground beef homogenate was passed through a glass wool filter. Large particulate matter was removed by the glass wool filter. To ensure the glass wool filter was not retaining the inoculated *E. coli*, the ground beef homogenate was plated before and after exposure to the filter. The *E. coli* concentration on the pre-filter plate and post-filter plater were approximately equal. The filtered ground beef homogenate was then flowed through the assay reaction chamber and the working electrode (onto which the goat anti-*E. coli* antibodies (analyte capturing molecule) had been bound as described above). After the ground beef homogenate passed through the assay reaction chamber, the analyte detector, 5 ml of $2.7 \times 10^{-9}$ M BacTrace anti-*Escherichia coli* O157:H7 antibody, peroxidase-labeled was flowed through the sample treated GFEs. The eluent was collected and then reapplied to each respective GFE and allowed to react for 60 min (with the valve closed) at room temperature. Following elution, the electrodes were rinsed twice with 5 mL PBST. Next, 5 mL of TMB $H_2O_2$ solution was applied to the GFEs and allowed to react for 20 min in the dark. Then 5 mL of the stop solution (1 M $H_2SO_4$) were added to the container and incubated for 5 min. The electrochemical response was monitored for the following concentrations of *E. coli* inoculation: $10^2$, $10^3$, $10^4$, and $10^6$. The current measured approximately −40 μA, −80 μA, −125 μA, and −375 μA, respectively.

In the current disclosure, the terms "approximately" and "about" refers to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim as follows:

1. A system for detecting an analyte in a sample, the system comprising:
   at least one assay reaction chamber;
   a potentiostat;
   a counter electrode; and
   a reference electrode;
   wherein the potentiostat is in electronic communication with the counter electrode, the reference electrode, and the at least one assay reaction chamber;
   each assay reaction chamber comprising: a porous working electrode having a plurality of analyte capturing molecules specific for the analyte being bound on the surface of the porous working electrode to provide a capture surface on the porous working electrode, through which the sample flows, an ingress opening through which the sample is capable of entering the assay reaction chamber, and an egress opening through which the sample is capable of exiting the assay reaction chamber; the porous working electrode having a porosity ranging from approximately 25% to approximately 90% and a surface area to volume ratio ranging from approximately 0.25 m2 g and approximately 10 m2/g, and being positioned within a lower portion of the assay reaction chamber;
   wherein the porous working electrode having the analyte capturing molecules is located on a bottom of the assay reaction chamber, the porous working electrode spans the assay reaction chamber and surrounds the egress opening to form a barrier between the ingress opening and the egress opening such that the sample must flow through the barrier to reach the egress opening;
   wherein the reference electrode and the counter electrode are on the inside wall of each of the assay reaction chamber and are situated above the porous working electrode;
   and free within the assay reaction chamber a plurality of analyte-detector molecule comprising an enzyme label and a substrate for the enzyme label,
   wherein the system is structured so that as the sample flows through pores of the porous working electrode, the analyte-capturing molecules specifically bind to any analyte present in the sample and generate an electric current when the plurality of analyte-detector molecules and the substrate are added to the reaction chamber; the electric current is being generated from the enzymatic reaction of the enzyme on the substrate from the analyte detector molecules that is bound to the analyte captured by the analyte-capturing molecule;
   the electric current is transmitted to the potentiostat, the presence and quantity of the electric current indicating a presence of the analyte in the sample.

2. The system of claim 1 wherein the analyte capturing molecules are selected from a group consisting of proteins, polynucleotides, bacteria, and viruses.

3. The system of claim 1, further comprising a flow control valve in fluid communication with the assay reaction chamber, wherein the flow control valve controls the sample's flow rate through the capture surface.

4. The system of claim 1, further comprising a waste reservoir in fluid communication with the flow control valve.

5. The system of claim 1, further comprising a sample reservoir upstream of the assay reaction chamber and in fluid communication with the assay reaction chamber.

6. The system of claim 1, further comprising a filter upstream of the assay reaction chamber and in fluid communication with the sample reservoir and the assay reaction chamber.

7. The system of claim 1, further comprising a pump, wherein the pump is in fluid communication with the assay reaction chamber.

8. The system of claim 1, wherein the assay reaction chamber comprises a first opening in a wall of the assay reaction chamber for the reference electrode to be in electronic communication with the potentiostat via a first connector, and a second opening in the wall of the assay reaction chamber for the counter electrode to be in electronic communication with the potentiostat via a second connector, wherein the first opening and the second opening are filled with an electronic fill material.

9. The system of claim 1 wherein the working electrode is comprised of a carbon-based material.

10. The system of claim 1 wherein the working electrode is comprised of a polymer containing graphite material.

11. The system of claim 1 wherein the working electrode is comprised of a graphite felt material.

12. The system of claim 1 wherein the working electrode is comprised of a polymer-carbon allotrope.

13. The system of claim 1 wherein the working electrode is comprised of a glassy carbon electrode.

14. The system of claim 8, wherein a bonding pad is screen-printed over the electronic fill material on an outside of the assay reaction chamber.

* * * * *